United States Patent [19]

Cavezzan et al.

[11] Patent Number: 4,873,305
[45] Date of Patent: Oct. 10, 1989

[54] TIN MONOCHELATE CATALYSIS OF ORGANOPOLYSILOXANE COMPOSITIONS

[75] Inventors: Jacques Cavezzan; Jean-Marc Frances, both of Villeurbanne; Claude Millet, Saint-Priest, all of France

[73] Assignee: Rhone-Poulenc Chimie, Courbevoie, France

[21] Appl. No.: 212,184

[22] Filed: Jun. 27, 1988

[30] Foreign Application Priority Data

Jun. 25, 1987 [FR] France ................. 87 09178

[51] Int. Cl.$^4$ .............................. C08G 77/06
[52] U.S. Cl. ..................... 528/18; 524/588; 524/859; 524/860; 528/901
[58] Field of Search ............ 528/18, 901; 524/860, 524/859, 588

[56] References Cited

U.S. PATENT DOCUMENTS 4,517,337  5/1985  Lockhart et al. ................. 524/859
4,554,310  11/1985  Wengrovius et al. ............... 528/18

OTHER PUBLICATIONS

Chemical Abstracts, vol. 82, No. 1, Jan. 6, 1975, 4375v.
Chemical Abstracts, vol. 82, No. 21, May 26, 1975, 140265n.
Journal of Organometallic Chemistry, vol. 185 (1980), pp. 209–217.

Primary Examiner—Melvyn I. Marquis
Attorney, Agent, or Firm—Burns, Doane, Swecker & Mathis

[57] ABSTRACT

Organopolysiloxane compositions curable into elastomeric state, whether in single- or two-component form, comprise an $\alpha,\omega$-dihydroxypolydiorganopolysiloxane oil, a crosslinking agent therefor, optionally, inorganic fillers and an adhesion promoter, and a catalytically effective amount of a pentacoordinated tin monochelate produced by reacting a tin oxide with a $\beta$-dicarbonyl compound and a carboxylic acid.

6 Claims, No Drawings

TIN MONOCHELATE CATALYSIS OF ORGANOPOLYSILOXANE COMPOSITIONS

BACKGROUND OF THE INVENTION

1. Field of the Invention

The present invention relates to novel curable polyorganosiloxane compositions, and, more especially, to such novel polyorganosiloxane compositions containing a catalytically effective amount of a tin monochelate crosslinking catalyst produced by reacting a $\beta$-dicarbonyl compound with a tin oxide and an organic carboxylic acid.

2. Description of the Prior Art

Many tin compounds have heretofore been proposed this art as a catalyst for crosslinking polyorganosiloxane compositions and, in particular, RTV compositions (room temperature vulcanizable compositions), in a single pack or in two packs, otherwise known as single- or two-component compositions.

The most widely used compounds are tin carboxylates such as tributyltin monooleate, tin 2-ethylhexanoate or dialkyltin dicarboxylates such as dibutyltin dilaurate and dibutyltin diacetate (see Noll *Chemistry and Technology of Silicones*, page 337, Academic Press, 1968 —2nd edition).

In U.S. Pat. No. 3,186,963, such a tin catalyst is described which is the reaction product of a dialkyldialkoxysilane with a dialkyltin carboxylate.

In Belgium Patent No. 842,305, the catalyst is the reaction product of an alkyl silicate or of an alkyltrialkoxysilane with dibutyltin diacetate.

And in U.S. Patent No. 3,708,467, a catalyst system is described which is a mixture of certain tin salts with a specific titanium chelate, in a single-component composition.

Lastly, in U.S. Pat. Nos. 4,517,337 and 4,554,310 the use of diorganotin bis($\beta$-diketone) is described for the crosslinking of neutral single-component compositions (U.S. Pat. Nos. 4,517,337 and 4,554,310) or for single- and two-component compositions (EP-A-147,323).

Although EP-A-147,323 represents a significant advance in the quest for a tin catalyst useful for both single- and two-component compositions, it has become apparent that diorganotin bis($\beta$-diketonates) exhibit a core I0 setting time which is a little too slow, particularly in the case of the two-component compositions.

The problem which typically arises in the case of the single-component compositions is essentially that of storage stability and of the retention of physicochemical properties (extrudability, pourability, setting time) of the composition and maintaining these properties by the reticulate (mechanical properties, hardness, elongation, tear strength, adhesiveness, and the like).

Thus, need exists in this art for a catalyst which crosslinks very rapidly on exposure to atmospheric moisture, not only on the surface thereof, but which at the same time provides a thorough crosslinking uniformly therethrough which is as complete as possible, and which is also active in minor amounts, while reducing to the minimum the reticulate degradation reactions which are inherent in the presence of tin.

With regard to the three-dimensional shaped article or reticulate thus obtained, the same problems as exist in the case of the single-component compositions also exist in the case of the two-component compositions, but, in addition, the exposure or open time (that is to say, the time during which the composition may be employed after mixing without hardening) must be sufficiently long to permit its effective use, but sufficiently short to produce a molded object capable of being handled not later than 24 hours after the production thereof.

This catalyst must therefore provide a good compromise between the open time of the catalyzed mixture and the time after which the molded object can be handled. In addition, the catalyst must impart to the catalyzed mixture a spreading time which does not vary as a function of the storage period.

SUMMARY OF THE INVENTION

Accordingly, a major object of the present invention is the provision of an improved catalyst system adapted for the crosslinking of both the single- and two-component elastomer compositions.

Another object of the present invention is the provision of an improved catalyst system which simultaneously meets the storage, use and crosslinking constraints common to both types of elastomer compositions, while addressing the specific problems presented by each, without, however, initiating detrimental secondary effects in either case.

Briefly, the present invention features improved organopolysiloxane compositions comprising, on the one hand, a silicone base polymer capable of being cured into an elastomer by a polycondensation reaction beginning at ambient temperature and, on the other hand, a catalytically effective amount of a monochelate of pentacoordinated tin of valency IV, of the formula:

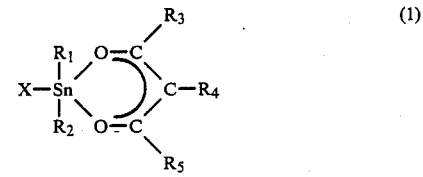

in which:

the symbols $R_1$ and $R_2$, which may be identical or different, are each an optionally substituted, monovalent $C_1$–$C_{18}$ hydrocarbon radical, and preferably are:

(i) $C_1$—$C18$ alkyl radicals, halogenated or otherwise, such as methyl, ethyl, propyl, isopropyl, butyl, isobutyl, secondary butyl, tert-butyl, pentyl, hexyl, heptyl, 2-ethylhexyl, octyl, decyl, dodecyl, octadecyl, chloromethyl and 2,5-dichloroethyl radicals;

(ii) $C_2$—$C18$ alkenyl radicals, halogenated or otherwise, such as vinyl, allyl, methallyl, 2-butenyl, 2-pentyl, 3-octenyl, 5-fluoro-2-pentenyl and pentadecenyl radicals;

(iii) $C_4$—$C10$ cycloalkyl radicals, halogenated or otherwise, such as cyclopentyl, cyclohexyl, methylcyclohexyl, cyclooctyl, 3,4-dichlorocyclohexyl and 2,6-dibromocycloheptyl radicals;

(iv) $C_6$—$C15$ mononuclear aryl radicals, halogenated or otherwise, such as phenyl, tolyl, xylyl, cumenyl, chlorophenyl, dichlorophenyl, trichlorophenyl, difluorophenyl and trifluoromethylphenyl radicals;

(v) $C_7$—$C15$ mononuclear arylalkyl radicals, halogenated or otherwise, such as phenylmethyl, phenylethyl, phenylpropyl and trifluoromethylphenylethyl radicals;

the symbols $R_3$ and $R_5$, which may be identical or different, are each one of the radicals $R_1$ or $R_2$, a hydrogen atom, a cyanoalkyl radical containing a $C_2$—$C_4$ alkyl moiety, a $C_1$—$C_5$ alkoxy radical or an -Si($R_1$)$_3$ silyl radical (cyanoethyl, cyanopropyl and cyanobutyl are exemplary of such cyanoalkyl radicals, and ethoxy and propoxy radicals are exemplary of the alkoxy radicals);

the symbol $R_4$ is a hydrogen atom, or an optionally halogenated $C_1$—$C_8$ hydrocarbon radical, with the proviso that $R_4$ and $R_5$ may together form, with the carbon atoms from which they depend, a $C_5$—$C_{12}$ cyclic hydrocarbon radical, or an optionally substituted such cyclic radical bearing at least one chloro, nitro and/or cyano substituent, for example $R_4$ is an alkyl radical, halogenated or otherwise, such as the methyl, ethyl, propyl, butyl, hexyl and octyl radicals, or a mononuclear aryl radical, halogenated or otherwise, such as the phenyl, tolyl, chlorophenyl and dichlorophenyl radicals, or $R_4$ is a ring member of one of the formulae:

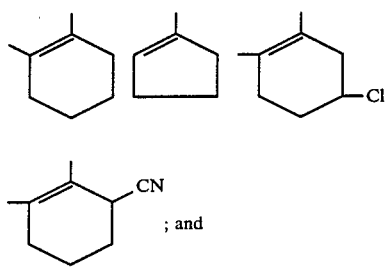

the symbol X is a monocarboxylate radical of the formula $R_6COO$ wherein $R_6$ has the same definition as $R_1$ above and preferably is a linear or branched chain $C_1$—$C_{18}$ alkyl radical.

DETAILED DESCRIPTION OF THE PREFERRED EMBODIMENTS OF THE INVENTION

More particularly according to the present invention, each of the monochelates of formula (1) is believed to be a novel compound.

These monocheates may be identified by the analytical techniques of NMR spectroscopy ($^{119}$Sn, $^{13}$C and $^1$H nuclear magnetic resonance), by mass spectroscopy and by measurement of the Mossbauer effect.

It has been found, however, that in the present state of the art of analytical techniques, the $^{119}$Sn NMR analytical method such as described, in particular, in the article by Peter J. Smith, *Chemical Shifts of $^{119}$Sn Nuclei in Organotin Compounds*, page 291 et seq, published in the *Annual Reports on NMR Spectroscopy*, volume 8, 1978, Academic Press, is a method which is by itself sufficiently accurate to characterize the various tin compounds present within a mixture, particularly within a reaction mixture, and to make it possible to determine the chemical formulae of most of these compounds.

The fundamental parameter evaluated by $^{119}$Sn NMR is the value of the chemical shift, expressed in parts per million (ppm) relative to a reference (generally tetramethyltin).

The value of the chemical shift is particularly sensitive to the electronegativity of the groups carried by the tin and to the change in the coordination number of the tin atom. Specific studies of characterization of organostannic derivatives using $^{119}$Sn NMR are described in particular by A. G. Davies and P. J. Smith, *Comprehensive Organo-metallic Chemistry*, 11 Tin, pages 523 to 529 and by J. Otera, *J. of Organomet. Chem.*, 221, pages 57–61 (1981).

The monochelates of formula (1) are prepared by reacting (a) a tin oxide of the formula:

$$R_1R_2SnO \qquad (2)$$

with, (b) a β-dicarbonyl compound of the formula:

or, more simply, having the abbreviated formula CH, and with (c) an organic carboxylic acid of the formula:

$$XH \qquad (4)$$

in which formulae $R_1$, $R_2$, $R_3$, $R_4$, $R_5$ and X are as defined above.

This reaction may be carried out in bulk or in an organic solvent (for example cyclohexane), with removal of water at the reflux temperature of the solvent employed According to this process, the starting materials of formulae (3) and (4) are reacted in a molar ratio (3)/(4) of from 0.01 to 100, preferably from 0.1 to 10, and more preferably from 0.4 to 2.5.

Furthermore, the compound (2) is used in amounts such that the molar ratio (2)/[(3) +(4)]ranges from 1/0.8 to ⅓.

The process of the invention is carried out simply by mixing the starting materials (1), (2) and (3) in a closed reactor in the absence of atmospheric moisture, with the removal of water. The reaction can take place beginning at ambient temperature. It is desirable, however, to raise the temperature of the reaction mixture to a value which generally ranges from 70° to 120° C. to accelerate the reaction kinetics and/or to remove the water formed and/or to solubilize a starting material which is in the solid state at ambient temperature.

The water formed may be removed by any known means, particularly by distilling the reaction mixture at a reduced pressure of from 0.01 to 10 kPa for a period of time which depends on the quality of the vacuum established.

The water formed may also be removed by azeotropic distillation at the reflux temperature of the solvent employed.

In one embodiment of the invention, the reaction of the starting materials of formulae (2), (3) and (4) may be carried out, not in a single stage, but in two stages.

During the first stage, the tin oxide of formula (2) is reacted with the acid of formula (4) to produce, after removal of the water formed, a distannoxane of formula (5):

$$XR_1R_2SnOSnR_1R_2X \qquad (5)$$

in which X, $R_1$ and $R_2$ are as defined above.

During the second stage, the distannoxane of formula (5) is reacted with the β-dicarbonyl compound of formula (3) and the desired reaction mixture is obtained after removal of the water formed, comprising the tin monochelate of formula (I).

The conditions in which these two stages are carried out are analogous to those which are employed in the case of the single-stage process.

The molar ratio (2)/(4) is preferably equal or very close to 1 and the molar ratio of (5)/(3) generally ranges from 1 to 1.5.

Exemplary of tin oxides of formula (2) are dimethyltin oxide, diethyltin oxide, dipropyltin oxide, dibutyltin oxide, di(2-ethylhexyl)tin oxide, dilauryltin oxide, dipropenyltin oxide, diphenyltin oxide, ditolyltin oxide, methyletbyltin oxide and phenylbutyltin oxide.

Exemplary of the β-dicarbonyl compounds, β-diketones and β-ketoesters of formula (3) are 2,4-heptanedione, 2,4-decanedione, 2-methyl-2-decene-6,8-dione, 2-methyl-2-nonene-6,8-dione, 1-stearoyl-2-octanone, triacetylmethane, ethyl 7,9-dioxodecanoate, benzoylacetone, 1-benzoyl-2-octanone, 1,4-diphenyl-1,3-butanedione, stearoylacetophenone, palmitoylacetophenone, 1-benzoyl-4-methyl-2-pentanone, benzoyloctacosanoylmethane, 1,4-bis(2,4dioxobutyl)benzene, paramethoxybenzoylstearoylmethane, 2-allyl-1-phenyl-l,3-butanedione, 2-methyl-2acetylacetaldehyde, benzoylacetaldehyde, acetoacetyl-3cyclohexene, bis(2,6-dioxocyclohexyl)methane, 2-acetyl-l-oxo-1,2,3,4-tetrahydronaphthalene, 2-palmitoyl-1-oxo-1,2,3,4tetrahydronaphthalene, 1-oxo-2-stearoyl-1,2,3,4tetrahydronaphthalene, 2-acetyl-1-cyclohexanone, 2-benzoyl-1-cyclohexanone, 2-acetyl-l,3-cyclohexanedione, dibenzoylmethane, tribenzoylmethane, bis(paramethoxybenzoyl)methane, 1-(N-phenylcarbamoyl)-1-benzoylacetone, 1-(N-phenylcarbamoyl)-1-acetylacetone, ethyl acetylacetate, acetylacetone and 1,1,1-trifluoro-3benzoylacetone.

These various β-diketones of formula (3) are typically prepared by various known procedures, such as those described in *Organic Reactions* by R. Adams et al (1954 edition, volume VIII, pages 59 et seq). Certain more specific syntheses are described in *Rec. Trav. Chim. Pays-Bas*, (1897), volume 16, pages 116 et seq, by M. J. Kramers, in *J. Chem. Soc.*, (1925), volume 127, pages 2891 et seq, by G. T. Morgan et al, or in *J. Chem. Soc.*, (1941), pages 1582 et seq, by R. Robinson and E. Seijo.

Exemplary of the carboxylic acids of formula (4), representative are:

(i) saturated carboxylic acids such as formic, acetic, propionic, butyric, isobutyric, valeric, isovaleric, pivalic, lauric, 2-ethylhexanoi-c, myristic, palmitic and stearic acids and versatic ® acids, which are mixtures of saturated tertiary monocarboxylic acids containing, overall, the same number of carbon atoms, which generally ranges from 8 to 12;

(ii) unsaturated carboxylic acids such as acrylic, propiolic (CH≡C—COOH), methacrylic, crotonic, isocrotonic, oleic and maleic acids;

(iii) aromatic carbocyclic acids such as benzoic, phthalic, isophthalic and terephthalic acids; and (iv) organic dicarboxylic acids.

The monochelate of formula (1) may be obtained essentially pure or in equilibrium with the starting materials and/or the reaction by-products and, in this case, it has been demonstrated in accordance with the invention that the equilibrium reaction mixture is capable of being employed in a catalytically effective amount for curing the silicone bases.

Using $^{119}$Sn NMR, it is found that, in general, in addition to the pentacoordinated monochelate $R_1R_2SnCX$, the equilibrium reaction mixture contains the di-stannoxane $XR_1R_2SnOSnR_1R_2X$, the diorganotin di-carboxylate or dihalide $R_1R_2SnX_2$, and the diorganotin bischelate $R_1R_2SnC_2$, as tin compound. When a molar ratio of starting materials (3)/(4) ranging from 0.5 to 1.5, and a molar ratio (2)/[(3) +(4)]ranging from 1/1 to 1/2.5 are employed, the concentrations of the constituents of the reaction mixture in molar %, calculated in gram-atoms of tin metal are, in principle:

$R_1R_2$ SnCX 30 to 95
$R_1R_2$ SnX$_2$ 30 to 5
$R_1R_2$SnC$_2$ 30 to 0
XR$_1$R$_2$SnOSnR$_1$R$_2$X 10 to 0

Unless otherwise indicated, all percentages and parts are given herein by weight.

The monochelate of formula (1) or the equilibrium reaction mixture, referred to hereinafter as the tin catalyst according to the invention, is stable in storage in a closed container, at ambient temperature.

It is used to permit or facilitate the curing of the organopolysiloxane base to a silicone elastomer, beginning at ambient temperature.

These bases, which cure (crosslink) by polycondensation reactions, are well known to this art. After having been catalyzed, in most cases by means of a metallic derivative of a carboxylic acid, they are utilized for the manufacture of seals, of water-repellent coatings, of molds, of coating materials, for the adhesive bonding and the assembly of the widest variety of materials, for coating organic and inorganic fibers, and the like.

These bases are described in detail, in particular, in many patents and they are available commercially.

These silicone bases may be single-component, that is to say, packaged in a single pack that is stable in storage in the absence of moisture and capable of being used in the presence of moisture, in particular of moisture contributed by the surrounding air or by the water generated within the base when it is used.

These single-component bases are generally of three types, as described in further detail below, and are catalyzed by the incorporation of a catalytically effective amount of the monochelate of formula (1) or of the equilibrium mixture containing the product of formula (1). This catalytically effective amount is on the order of 0.0001 to 5 parts, preferably from 0.01 to 3 parts per 100 parts of the single-component base.

Other than the single-component bases, it is also possible to employ two-component bases, that is to say, those packaged in two packs, which cure as soon as the tin catalyst is incorporated. They are packaged in two separate fractions, it being possible for one of the fractions, for example to contain only the tin catalyst or the mixture of the catalyst with the crosslinking agent.

The catalytically effective amount of tin catalyst is on the order of 0.01 to 10 parts, preferably from 0.1 to 5 parts per 100 parts of the two-component base.

As already indicated above, single-component and two-component silicone bases which cure (crosslink) via polycondensation reactions are described in detail in the literature and are available commercially.

These bases are generally prepared from the following constituents:

(A) 100 parts of an α,ω-dihydroxypolydiorganosiloxane polymer, having a viscosity of 500 to 1,000,000 mPa.s at 25° C., comprising recurring units of the formula $(R_2)SiO$ where the symbols R, which may be identical or different, are hydrocarbon radicals containing from 1 to 10 carbon atoms, optionally substituted by halogen atoms or cyano groups;

(B) 0.5 to 20 parts of a crosslinking agent selected from among organosilicon compounds containing more than two hydrolyzable groups bonded to silicon atoms, per molecule;

(C) 0 to 250 parts of inorganic fillers; and (D) 0 to 20 parts of an adhesion promoter.

The radical R is typically methyl, ethyl, propyl, phenyl, vinyl or a 3,3,3-trifluropropyl radical, at least 80% of the groups R being methyl.

A first type of single-component formula results from mixing the polymer A with a crosslinking agent B, which advantageously is a silane of the formula:

$$R_a Si(Z)_{4-a} \qquad (6)$$

in which R is as defined above for the polymer A, and Z is a hydrolyzable group advantageously selected from among N-substituted amino, N-substituted amido, N,N-disubstituted aminoxy, ketiminoxy, aldiminoxy, alkoxy, alkoxyalkylenoxy, enoxy and acyloxy groups, and a denotes 0 or 1.

Single-component bases of this type are described in detail, particularly in European Patent Applications EP-A-141,685 and EP-A-147,323, hereby incorporated by reference.

The most widely used compositions are those in which Z is an acyloxy and ketiminoxy group, which are described in greater detail in European Patent Application EP-A-102,268, also hereby incorporated by reference.

Two-component flowing compositions, in which Z is an acyloxy group, and whose crosslinking is accelerated by the addition of an alkaline earth metal hydroxide or phosphate are described in European Patent Applications EP-A-118,325 and EP-A-117,772, also hereby incorporated by reference.

In a second type of single-component base, the starting point is not a mixture of A and B but the product $A_1$ of reaction of A with B. In general, the hydrolyzable group is an alkoxy group and the composition additionally contains from 0 to 15 parts of crosslinking agent B per 100 parts of functionalized polymer $A_1$.

The reaction of A with B can be carried out in the presence of various catalysts such as an organic amine (U.S. Pat. No. 3,542,901), an organic titanium derivative (U.S. Pat. No. 4,111,890), a carbamate (European Patent Application EP-A-210,402) and an N,N-disubstituted hydroxylamine (European Patent Application EP-A-70,786).

To these single-component bases there may be added adhesion promoters D, selected from among organosilicon compounds simultaneously bearing, on the one hand, organic groups substituted by radicals selected from among amino, ureido, isocyanate, epoxy, alkenyl, isocyanurate, hydantoyl, guanidino and mercaptoester radicals and, on the other hand, hydrolyzable groups, generally alkoxy groups bonded to the silicon atoms. Examples of such adhesion promoters are described in U.S. Pat. Nos. 3,517,001, 4,115,356, 4,180,642, 4,273,698 and 4,356,116, and in European Patent Applications EP-A-31,996 and EP-A-74,001.

A third type of single-component bases are those prepared by mixing 100 parts of polymer A, from 0.5 to 20 parts of crosslinking agent B which is a polyalkoxysilane (formula 4), Z=alkoxy or alkoxyalkyleneoxy, from 0 to 250 parts of inorganic fillers and from 0.5 to 15 parts of a compound $D_1$ selected from among:

(i) $D_{1-a}$: a primary organic amine having a pKb of less than 5 in aqueous medium, an aminoorganosilane and an aminoorganopolysiloxane bearing at least one $C_1$–$C_{15}$ organic group linked by a Si-C bond to the silicon atom per molecule, and substituted by at least one amino radical, and at least one $C_1$–$C_5$ alkoxy or $C_3$–$C_6$ alkoxy alkyleneoxy radical; and (ii) $D_{1-b}$: an organic titanium or zirconium derivative bearing an organoxy and/or β-diketonato group.

Single-component bases comprising $D_{1-a}$ are described in European Patent Application EP-A-21,859, and those comprising $D_{1-b}$ are described in French Patents FR-A-2,121,289 and FR-A-2,121,631, also hereby incorporated by reference.

The two-component bases are formed by mixing:

(a) 100 parts of polymer (A);

(b) 1 to 20 parts of a crosslinking agent selected from among a silane of formula (6) above, and the products of partial hydrolysis of the silane of formula (4);

(c) 0 to 150 parts of inorganic fillers; and (d) 0 to 20 parts of an adhesion promoter.

These compositions are well known to this art; in particular, they are described in European Patent Applications EP-A-10,478, EP-A-50,358 and EP-A-184,966 and in U.S. Pat. Nos. 3,801,572 and 3,888,815.

The adhesion promoter employed may be the silanes D employed in the case of the single-component bases and silanes bearing a morpholino group (EP-A-184,966) or an organic radical comprising a tertiary nitrogen atom (U.S. Pat. Nos. 3,801,572 and 3,888,815).

The products of partial hydrolysis of the alkoxysilanes of formula (4), which are usually referred to as alkyl polysilicates, are well-known products which exhibit the property of dissolving in the usual hydrocarbon solvents such as toluene, xylene, cyclohexane and methylcyclohexane; the most widely used material is ethyl polysilicate 40 ® with a silica content of 40%, a value obtained after total hydrolysis of the ethoxy radicals.

The inorganic fillers (c) employed in the case of the single- and two-component bases are very finely divided materials whose mean particle diameter is below 0.1 micrometer. These fillers include pyrogenic silicas and precipitated silicas; their BET specific surface area is generally greater than 40 $m^2/g$.

If desired, these fillers may be in the form of more coarsely divided materials, with a mean particle diameter greater than 0.1 micrometer. Examples of such fillers which are representative are ground quartz, diatomaceous silicas, calcium carbonate, calcined clay, rutile-type titanium dioxide, iron, zinc, chromium, zirconium and magnesium oxides, the various forms of alumina (hydrated or otherwise), boron nitride, lithopone, barium metaborate, barium sulfate and ballotini; their specific surface area is generally below 30 $m^2/g$.

These fillers may have been surface-modified by treatment with the various organosilicon compounds usually employed for this purpose. Thus, these organosilicon compounds may be organochlorosilanes, diorganocyclopolysiloxanes, hexaorganodisiloxanes, hexaorganodisilazanes or diorganocyclopolysilazanes (French Patents Nos. FR-A-1,126,884, FR-A-1,136,885, FR-A-1,236,505, British patent No. GB-A-1,024,234). In most cases, the treated fillers contain from 3 to 30% of their weight of organosilicon compounds.

The fillers may be a mixture of a number of types of fillers of different particle size distribution; for example, they may comprise 30 to 70% of finely divided silicas with a BET specific surface area greater than 40 $m^2/g$ and of 70 to 30% of more coarsely divided silicas with a specific surface area below 30 m²/g.

The tin catalyst according to the invention is more particularly effective in the case of the single- and two-component silicone bases where the crosslinking agent (B) of formula (6) contains radicals Z which are identical or different, selected from among alkoxy and alkoxyalkyleneoxy radicals of formulae $R_7O$ and $R_7OTO$ in which $R_7$ is a $C_1$—$C_4$ alkyl radical and T denotes a $C_2$—$C_4$ alkylene group.

In addition, in the case where the silicone base has two components, it is possible to use the product of partial hydrolysis of the crosslinking agent (B).

In addition to the fundamental constituents of the single-component and two-component bases, that is to say, (1) the diorganopolysiloxane polymers (A) and/or ($A_1$) blocked by a hydroxyl radical and/or alkoxyl radicals at the end of a chain, (2) the organosilicon crosslinking agents (B) bearing hydrolyzable groups, (3) the inorganic fillers and (4) the adhesion promoters (D), other ingredients may be introduced.

These ingredients include organosilicon compounds, chiefly polymers, which are capable of affecting the physical characteristics of the compositions according to the invention (formed by mixing the bases with the tin catalyst) and/or the mechanical properties of the silicone elastomers obtained using these compositions.

These compounds are well known; for example, they include:

(i) $\alpha,\omega$-bis(triorganosiloxy)diorganopolysiloxane polymers having a viscosity of at least 10 mPa.s at 25° C. in which the organic radicals bonded to the silicon atoms are methyl, vinyl and phenyl radicals, preferably at least 80% of the radicals are methyl radicals and not more than 3% are vinyl radicals; $\alpha,\omega$-bis(trimethylsiloxy)-dimethylpolysiloxane oils having a viscosity of 10 mPa.s at 25° C. to 1,500 mPa.s at 25° C. are preferably employed;

(ii) liquid, branched methylpolysiloxane polymers containing from 0.1 to 8% of hydroxyl groups bonded to the silicon atoms, comprising $(CH_3)SiO_{0.5}$, $(CH_3)_2SiO$ and $CH_3SiO_{1.5}$ recurring units distributed such as to provide a $(CH_3)_3SiO_{0.5}/(CH_3)_2SiO$ ratio of 0.01 to 0.15 and a $CH_3SiO_{1.5}/(CH_3)_2SiO$ ratio of 0.1 to 1.5;

(iii) $\alpha,\omega$-di(hydroxy)dimethylpolysiloxane oils having a viscosity of 10 to 300 mPa.s at 25° C. and $\alpha,\omega$-di(hydroxy)methylphenylpolysiloxane oils having a viscosity of 200 to 5,000 mPa.s at 25° C.; and (iv) diphenylsilanediol and 1,1,3,3-tetramethyldisiloxanediol.

The above $\alpha,\omega$-bis(triorganosiloxy)diorganopolysiloxane polymers may be completely or partly replaced by organic compounds which are inert towards the various constituents of the bases and which are miscible at least with the diorganopolysiloxane polymers (A) or ($A_1$). Specific examples of such organic compounds are mineral oils, petroleum cuts and polyalkylbenzenes obtained by the alkylation of benzene with long-chain olefins, particularly olefins containing 12 carbon atoms obtained by propylene polymerization. Organic compounds of this type appear, for example, in French Pat. Nos. FR-A-2,392,476 and FR-A-2,446,849.

Each of the above organosilicon compounds may be employed in a proportion of 1 to 150 parts, preferably 3 to 75 parts, per 100 parts of diorganopolysiloxanes (A) or ($A_1$).

Non-organosilicon ingredients may also be introduced, for example heat stabilizers. These compounds improve the heat resistance of the silicone elastomers. They may be carboxylic acid salts, rare-earth oxides and hydroxides and more especially ceric oxides and hydroxides, as well as from combustion titanium dioxide and various iron oxides. From 0.1 to 15 parts, preferably from 0.15 to 12 parts of heat stabilizers are advantageously employed per 100 parts of the diorganopolysiloxanes (A) or ($A_1$).

In the case of the single-component compositions, to produce the compositions according to the invention it is necessary to employ apparatus which enables the various fundamental constituents, to which the above-mentioned adjuvants and additives are added if desired, to be intimately mixed in the absence of moisture, with and without application of heat.

All these ingredients may be charged into the apparatus in any order of addition. Thus, the diorganopolysiloxane polymers (A) or ($A_1$) and the fillers (C) can first be mixed, and the crosslinkers (B), the compounds (D) and the tin catalyst can then be added to the resulting paste.

It is also possible to mix the polymers (A) or ($A_1$), the crosslinkers (B) and the compounds (D) and subsequently to add the fillers (C) and the tin catalyst. The mixtures may be heated during these operations to a temperature in the range 50°–180° C. at atmospheric pressure or at a reduced pressure in order to promote the elimination of volatile materials such as water and polymers of low molecular weight.

The compositions prepared in this manner may be employed as such or in the form of a dispersion in organic diluents. These diluents are preferably conventional commercial products selected from among:

(i) aliphatic, cycloaliphatic or aromatic hydrocarbons, halogenated or otherwise, such as n-heptane, n-octane, cyclohexane, methylcyclohexane, toluene, xylene, mesitylene, cumene, tetralin, decalin perchloroethylene trichloroethane tetrachloroethane, chlorobenzene and orthodichlorobenzene;

(ii) aliphatic and cycloaliphatic ketones such as methyl ethyl ketone, methyl isobutyl ketone, cyclohexanone and isophorone; and (iii) esters such as ethyl acetate, butyl acetate and ethylglycol acetate.

The quantities of diluents introduced must be sufficient to produce stable dispersions which spread easily on the substrates. These quantities depend essentially on the nature and on the viscosity of the initial organopolysiloxane compositions. They may consequently vary within wide proportions; nevertheless, formulation of dispersions containing from 15 to 85% by weight of diluents is recommended.

The single-component compositions according to the invention, which are used as such, that is to say, undiluted, or in the form of dispersions in diluents, are stable in storage in the absence of water and cure beginning at ambient temperature (after removal of the solvents in the case of dispersions) to form elastomers, in the presence of water.

After the compositions as such have been deposited onto solid substrates, in a moist atmosphere, it is found that a process of curing to elastomers takes place, proceeding from the outside towards the inside of the deposited mass. A surface skin forms first and then the crosslinking continues into the depth of the mass.

The complete formation of the skin, which manifests itself as a nonsticky surface feel, requires a period of time which can be in the range from 1 minute to 55 minutes; this time period depends on the relative humidity content of the atmosphere surrounding the compositions and on the ease of crosslinking of the latter.

Furthermore, the cure throughout the deposited layers, which must be sufficient to allow the elastomers formed to be demolded and handled, requires a longer period of time. This period depends, in fact, not only on the factors mentioned above in the case of the formation of a nonsticky feel, but also on the thickness of the deposited layers, which thickness generally ranges from 0.5 mm to several centimeters. This longer period of time may range from 10 minutes to 20 hours.

The single-component compositions may be employed for many applications, such as sealing in the building industry, the assembly of a very wide variety of materials (metals, plastics, natural and synthetic rubbers, wood, cardboard, earthenware, brick, ceramic, glass, stone, concrete, masonry components), the insulation of electrical conductors, coating of electronic circuits, and the production of molds used for the manufacture of objects made of synthetic resins or foams.

The above-mentioned dispersions of these compositions in the diluents can be employed for thin-layer impregnation of inorganic, synthetic, organic, metallic, woven or nonwoven products and articles, and coating of metal, plastic or cellulosic sheets. The deposition can be produced, for example, by dipping or by spraying; in the latter case, a spray gun is used which permits uniform coatings with a thickness of 5 to 300 μm to be obtained. After the spraying of the dispersions, the diluents evaporate off and the compositions released cure to a rubbery film.

The production of two-component compositions according to the invention is also carried out by mixing the various constituents in suitable apparatus. To obtain homogeneous compositions it is preferable to mix the polymers (A) with the fillers (C) first; the combination may be heated for at least 30 minutes to a temperature above 80° C. such as to complete the wetting of the fillers by the oils. The other constituents, namely, the crosslinking agents (B), the organic tin derivative and, if desired, various additives and adjuvants, and even water, can be added to the mixture obtained, which is preferably heated to a temperature below 80° C., for example on the order of ambient temperature.

Such compositions are not stable in storage and must therefore be used quickly, for example within a time interval of 40 minutes.

The various additives and adjuvants are the same as those introduced into the single-component compositions. In particular, the $\alpha,\omega$-bis(triorganosiloxy)diorganopolysiloxane polymers having a viscosity of at least 10 mPa.s at 25° C., in which the organic radicals bonded to the silicon atoms are methyl, vinyl and phenyl radicals, are representative. $\alpha,\omega$-(Trimethylsiloxy)dimethylpolysiloxane oils having a viscosity of preferably 20 mPa.s at 25° C. to 1,000 mPa.s at 25° C., are generally employed in a proportion not exceeding 150 parts per 100 parts of polymer (A).

The introduction of water in a proportion not exceeding 1 part per 100 parts of polymers (A) is recommended to promote the curing of the two-component compositions which are employed in thick layers whose thickness is, for example, greater than 2 cm.

This water addition is unnecessary if the fillers (C) contain enough of it. To facilitate its incorporation, water is preferably added in the form of a dispersion in a paste comprising, for example, the above-mentioned $\alpha,\omega$-bis(triorganosiloxy)diorganopolysiloxane oils and the fillers (C).

For packaging and storage, the two-component compositions cannot, therefore, contain all the fundamental constituents, namely, the polymers (A), the crosslinker (B), the fillers (C) and the tin catalyst (E). On an industrial scale, they must be formulated in the form of two components, each being stable in storage.

A first, storage-stable, component may, for example, comprise the constituents (A), (B) and (C); it is preferably prepared by introducing the crosslinking agents (B) into the homogeneous mixture produced by compounding the polymers (A) with the fillers (C).

The second component then comprises the tin catalyst.

Other ways of presenting the two-component compositions may be selected, for example, a first component containing the polymers (A) and the fillers (C), and a second component containing the crosslinking agents (B) and the tin catalyst.

In many applications it is preferable that each of the two components be sufficiently fluid such as to easily form compositions whose viscosity ranges, for example, from 10,000 to 800,000 mPa.s at 25° C. when mixed.

These compositions, which remain sufficiently fluid for at least 40 minutes, preferably for at least 80 minutes, after the mixing of the two components, can be employed more especially for the manufacture of silicone elastomer molds. They may, however, be employed for other applications such as coating electronic equipment and coating metallic or textile or cellulosic surfaces.

The molds which are manufactured are intended to reproduce articles made of cellular or noncellular materials formed from organic polymers. Among such materials, exemplary are polyurethanes, polyesters, polyamides, and polyvinyl chloride. The use of these molds for the reproduction of polyurethane articles is, however, recommended, since they withstand quite well attack by constituents of the mixtures used to produce polyurethane materials (in particular polyisocyanates).

The introduction of the tin catalyst according to the invention, at least partly comprising the tin monochelate, makes it possible to attain the best conditions of use in the case of the single- and two-component compositions. It makes it possible to subsequently produce elastomers having stable properties upon use thereof and with tensile properties which are stable over time which are independent of the age and of the storage conditions of the compositions.

In order to further illustrate the present invention and the advantages thereof, the following specific examples are given, it being understood that same are intended only as illustrative and in nowise limitative.

EXAMPLE 1

0.1 mole of dibutyltin oxide, 0.1 mole (20.1 g) of lauric acid, 21.33 g of 1-benzoyl-4-methyl-2-pentanone and 130 ml of cyclohexane were introduced in succession into a 250 ml three-necked round-bottomed flask fitted with a central stirrer, a condenser and a thermometer.

The mixture was heated under reflux for 2 hours under a nitrogen atmosphere and then most of the cyclohexane was distilled off until the reaction mass was at 90° C.

100 ml of cyclohexane and 2 ml of water were collected.

The reaction mixture was then concentrated in a rotary evaporator for 30 minutes at 70° C. under 0.27 kPa and 65 g of a light-yellow liquid were obtained, containing 53 mol % (calculated in gram-atoms of tin metal) of pentacoordinated tin monochelate, as determined by $^{119}$Sn NMR using the above-mentioned method described by Peter J. Smith.

The results are reported in Table I below.

EXAMPLES 2 to 16

The operating procedure of Example 1 was repeated, except that the reactants and/or the quantities introduced were changed.

The results obtained are reported in Table I below.

The reaction may be expressed schematically as follows:

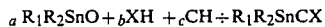

$$_a R_1R_2SnO + _bXH + _cCH \div R_1R_2SnCX$$

$$+ R_1R_2SnC2 + R_1R_2SnX_2 + H_2O$$

with a, b and c being the molar quantities which were introduced, of $R_2SnO$, XH and CH, respectively, XH is the acid introduced,
XH1: lauric acid,
XH2: versatic R acid,
XH3: $(CH_3)_3CCOOH$ (pivalic) acid,
XH4: 2-ethylhexanoic acid,
XH5: acetic acid,
XH6: benzoic acid,
XH7: chloroacetic acid,
CH1: 1-benzoyl-4-methyl-2-pentanone,
CH2: acetylacetone,
CH3: dibenzoylmethane,
CH4: 1,1,1-trifluoro-3-benzoyl acetone.

In Table I, columns PR1, PR2, PR3 and PR4 report the mol % calculated in gram-atoms of tin metal for the products present in the reaction mixture.

PR1: R1 R2 Sn CX
PR2: R1 R2 Sn X2
PR3: R1 R2 Sn C2
PR4: X R1 R2 Sn OSn R1 R2 X

TABLE I

| Example | R1 and R2 | a | XH | b | CH | c | PR1 | PR2 | PR3 | PR4 |
|---|---|---|---|---|---|---|---|---|---|---|
| 1 | C4H9 | 0.1 | XH1 | 0.1 | CH1 | 0.1 | 53.0 | 23.0 | 17.0 | 7.0 |
| 2 | C4H9 | 0.5 | XH1 | 0.5 | CH1 | 0.5 | 51.2 | 22.8 | 20.3 | 5.7 |
| 3 | C4H9 | 0.2 | XH1 | 0.2 | CH1 | 0.23 | 54.8 | 21.0 | 21.0 | 2.2 |
| 4 | C4H9 | 0.2 | XH1 | 0.23 | CH1 | 0.23 | 54.0 | 34.0 | 12.0 | 0 |
| 5 | C4H9 | 0.05 | XH2 | 0.05 | CH1 | 0.05 | 56.0 | 23.0 | 21.0 | 0 |
| 6 | C4H9 | 0.1 | XH3 | 0.1 | CH1 | 0.1 | 56.0 | 20.8 | 20.0 | 3.8 |
| 7 | C4H9 | 0.1 | XH4 | 0.1 | CH1 | 0.1 | 51.0 | 21.4 | 22.5 | 5.1 |
| 8 | C8H17 | 0.1 | XH4 | 0.1 | CH1 | 0.1 | 51.1 | 19.7 | 23.4 | 5.8 |
| 9 | C4H9 | 0.1 | XH5 | 0.1 | CH1 | 0.1 | 49.5 | 18.8 | 28.2 | 3.5 |
| 10 | C4H9 | 0.1 | XH5 | 0.1 | CH2 | 0.1 | 75.0 | 5.8 | 9.7 | 9.5 |
| 11 | C8H17 | 0.015 | XH1 | 0.015 | CH3 | 0.015 | 54.5 | 20.0 | 16.4 | 9.1 |
| 12 | C8H17 | 0.015 | XH1 | 0.020 | CH4 | 0.020 | 35.5 | 44.5 | 20.0 | 0 |
| 13 | C4H9 | 0.1 | XH6 | 0.1 | CH2 | 0.1 | 73.0 | 12.0 | 6.0 | 9.0 |
| 14 | C4H9 | 0.1 | XH6 | 0.1 | CH1 | 0.1 | 69.0 | 12.0 | 14.0 | 5.0 |
| 15 | C8H17 | 0.1 | XH1 | 0.1 | CH1 | 0.1 | 61.0 | 27.0 | 12.0 | 0 |
| 16 | C4H9 | 0.1 | XH7 | 0.1 | CH1 | 0.1 | 90.0 | 4.5 | 0 | 5.20 |

EXAMPLE 17

1 mole (360 g) of di-n-octyltin oxide, 1.2 mole (244.8 g) of 1-benzoyl-4-methyl-2-pentanone and 0.9 mole (129 g) of 2-ethylhexanoic acid were charged into a 1-liter three-necked round-bottomed flask fitted with a central stirrer, a condenser and a thermometer.

A clear yellow oil, having the following physicochemical characteristics, was obtained:
Viscosity at 25° C.: 163 mpa.s
Relative density at 25° C.: 1.081
Refractive index at 25° C. 1.521

EXAMPLES 18 to 20

The operations carried out were the same as in Example 16, except that the molar ratios a, b and c of the reactants were varied; the results obtained are reported in Table II below, where $R_1$, $R_2$, a, XH, b, CH, c, PR1, PR2, PR3 and PR4 have the same meanings as in Table I above.

TABLE II

| Example | R1 and R2 | a | XH | b | CH | c | PR1 | PR2 | PR3 | PR4 |
|---|---|---|---|---|---|---|---|---|---|---|
| 17 | C8H17 | 1 | XH4 | 0.9 | CH1 | 1.2 | 30.4 | 49.0 | 7.6 | 12.0 |
| 18 | C8H17 | 1 | XH4 | 1.5 | CH1 | 0.6 | 49.6 | 15.0 | 23.4 | 10.5 |
| 19 | C8H17 | 1 | XH4 | 1 | CH1 | 1 | 44.0 | 13.0 | 29.5 | 13.5 |
| 20 | C8H17 | 1 | XH4 | 0.6 | CH1 | 1.5 | 33.2 | 7.3 | 47.7 | 11.3 |

COMPARATIVE EXAMPLE 21 and EXAMPLES 22 to 26

A composition $P_1$ was prepared by mixing:

(i) 100 parts of an α,ω-dihydroxydimethylpolysiloxane oil having a viscosity of 10,000 mPa.s at 25° C.;

(ii) 70 parts of an α,ω-bis(trimethylsiloxy)dimethylpolysiloxane oil having a viscosity of 800 mPa.s at 25° C.;

(iii) 55 parts of a pyrogenic silica having a specific surface area of 300 m$^2$/g, treated with hexamethyldisilazane;

(iv) 50 parts of ground quartz having a mean particle diameter of 5 micrometers; and (v) 10 parts of a paste made up of 90 parts of the above-mentioned α,ω-dihydroxydimethylpolysiloxane oil, having a viscosity of 10,000 ma.s at 25° C., 5 parts of a pyrogenic silica having a specific surface area of 150 m$^2$/g and 5 parts of water.

The composition $P_1$ was catalyzed with a crosslinking system containing some of the catalysts C forming the subject of the preceding examples and partially hydrolyzed ethyl silicate.

The composition $P_1$ was catalyzed by mixing 100 parts of this composition with two parts of the crosslinking system consisting of 17.5% by weight of catalyst C and 82.5% by weight of partially hydrolyzed ethyl silicate. This crosslinking system was employed as such, freshly prepared ($\Delta t=0$) or after having been subjected to aging at 70° C. for a period $\Delta t$ of 72, 168 and 336 hours.

The spreading time (st) of the catalyzed composition was then determined by noting the time for which this composition remained in a sufficiently fluid state to spread under its own weight and thus to adopt the configuration of the internal volume of the receptacles into which it was poured.

The test employed for assessing the spreadability was as follows:

The freshly catalyzed composition (15 grams) was poured into an aluminum capsule of cylindrical shape with a diameter of 4 cm; after a time not exceeding 5 minutes its surface must be perfectly horizontal.

The catalyzed composition was converted into a silicone elastomer after several hours at ambient temperature; 24 hours (1 day) and 96 hours (4 days) after the preparation of this catalyzed composition the Shore A hardness of the elastomer formed was measured. The results relating to the spreading time (st) in minutes and the Shore A hardness values (SAH1 and SAH4) are reported in Table III below.

The catalyst in the comparative example was di-noctyltin di-2-ethylhexanoate.

The results are reported in Table III below, where C ex n shows that the tin catalyst employed was that obtained in Example n.

It was found that the catalysts according to the invention, in contrast to the control catalyst, endow the silicone elastomer with satisfactory hardness and spreading time values even after prolonged aging of the crosslinking system.

as the control catalyst in comparative Example 27 was di(n-octyl)tin dilaurate and the catalyst in Example 28 was that synthesized in Example 15 above.

The results obtained are reported in Table IV below.

It was found that the catalyst employed in Example 28, in contrast to the control catalyst in comparative Example 27, endows the silicone elastomer with satisfactory hardness and spreading time values even after prolonged aging.

TABLE IV

| EXAMPLE | 27 CONTROL | | | 28 C ex 15 | | |
|---|---|---|---|---|---|---|
| CATALYST | st | SAH1 | SAH2 | st | SAH1 | SAH2 |
| $\Delta t$ 0 | 160 | 17 | 26 | 95 | 20 | 26 |
| 72 | 195 | 17 | 25 | 95 | 20 | 25 |
| 144 | 100 | 19 | 27 | 100 | 20 | 25 |
| 288 | 90 | 18 | 26 | 100 | 20 | 25 |

COMPARATIVE EXAMPLE 29 and EXAMPLES 30 to 32

The purpose of these Examples was to demonstrate the better natural aging behavior of the elastomers obtained from 100 parts of composition $P_1$ of Example 21 to 26, catalyzed with 5 parts of a crosslinking system consisting of 17.5% by weight of catalyst C and 82.5% by weight of partially hydrolyzed ethyl silicate.

The catalyzed composition was deposited onto a polyethylene plaque, in the form of a layer having a thickness of 2 mm. After a period of 24 hours at rest in ambient air, the elastomer film obtained was demolded and was permitted to age at a temperature of 20° C. for various times (in months).

The Shore A hardness and the tear resistance TR (expressed in kN/m) of the film which had been subjected to the above-mentioned aging times were measured.

The results are reported in Table V below, where C ex n shows that the tin catalyst employed is that obtained in Example n. The control catalyst in Comparative Example 29 was di-n-octyltin di-2-ethylhexanoate.

TABLE III

| EXAMPLE | 21 CONTROL | | | 22 C ex 8 | | | 23 C ex 17 | | |
|---|---|---|---|---|---|---|---|---|---|
| CATALYST | st | SAH1 | SAH4 | st | SAH1 | SAH4 | st | SAH1 | SAH4 |
| $\Delta t$ 0 | 170 | 16 | 26 | 240 | 12 | 24 | 170 | 15 | 25 |
| 72 | 210 | 12 | 24 | | | | 180 | 16 | 26 |
| 168 | 290 | 6 | 23 | 235 | 13 | 24 | 160 | 14 | 25 |
| 336 | 310 | 5 | 23 | 200 | 17 | 23 | 170 | 15 | 25 |

| EXAMPLE | 24 C ex 18 | | | 25 C ex 19 | | | 26 C ex 20 | | |
|---|---|---|---|---|---|---|---|---|---|
| CATALYST | st | SAH1 | SAH2 | st | SAH1 | SAH2 | st | SAH1 | SAH2 |
| $\Delta t$ 0 | 170 | 15 | 25 | 240 | 13 | 24 | 150 | 18 | 27 |
| 72 | 170 | 17 | 25 | | | | 170 | 16 | 24 |
| 168 | | | | 235 | 13 | 24 | 180 | 16 | 25 |
| 336 | 230 | 15 | 26 | 200 | 17 | 24 | 200 | 16 | 26 |

COMPARATIVE EXAMPLE 27 and EXAMPLE 28

The operating procedure of the preceding Examples 21 to 26 was repeated, except that the catalyst employed

TABLE V

| | | AGING PERIOD | | | | | | | | |
|---|---|---|---|---|---|---|---|---|---|---|
| | | 0 MONTHS | | 1 MONTH | | 3 MONTHS | | 7 MONTHS | | 11 MONTHS | |
| EXAMPLE | CATALYST C ex n | SAH | TR | SAH | TR | SAH | TR | SAH | TR | SAH | TR |
| 29 | CONTROL | 38 | 25 | 41 | 25 | 42 | 24 | 43 | 15 | 45 | 6 |
| 30 | C ex 18 | 38 | 24 | 40 | 24 | 41 | 24 | 40 | 23 | 43 | 10 |
| 31 | C ex 17 | 35 | 24 | 37 | 21 | 39 | 23 | 38 | 22 | 38 | 23 |

TABLE V-continued

| EXAMPLE | CATALYST C ex n | AGING PERIOD | | | | | | | | |
|---|---|---|---|---|---|---|---|---|---|---|
| | | 0 MONTHS | | 1 MONTH | | 3 MONTHS | | 7 MONTHS | | 11 MONTHS |
| | | SAH | TR | SAH | TR | SAH | TR | SAH | TR | SAH | TR |
| 32 | C ex 20 | 37 | 24 | 40 | 25 | 41 | 25 | 40 | 23 | 43 | 17 |

From Table V, it will be seen that better stability of the elastomer was obtained with a catalyst in accordance with the invention.

COMPARATIVE EXAMPLE 33 and EXAMPLE 34

The following ingredients were triturated in a kneader:
(i) 100 parts of an α,ω-dihydroxydimethylpolysiloxane oil having a viscosity of 70,000 mPa.s at 25° C.;
(ii) 20 parts of a bis(trimethylsiloxy)dimethylpolysiloxane oil having a viscosity of 100 mPa.s at 25° C.;
(iii) 130 parts of calcium carbonate having a mean particle diameter of 5 micrometers; and
(iv) 10 parts of pyrogenic silica having a specific surface area of 50 m$^2$/g.

When the mass was homogeneous, all the solution produced by mixing the following ingredients was added to it:
5.5 parts of silane of formula Si(OCH$_2$CH$_2$OC$_2$H$_5$)$_4$;
2.5 parts of silane of formula (CH$_3$O)$_3$Si(CH$_2$)$_3$-NH-CH$_2$CH$_2$NH$_2$;
0.040 part of the organic tin derivative which was prepared according to the procedure of Example 16 above.

The single-component composition thus obtained was stored in the absence of moisture in sealed aluminum tubes (Example 34); another composition, identical with the preceding, was prepared, except that the organic tin derivative employed was only dibutyltin dilaurate, and the quantity employed was identical, namely, 0.040 part (comparative Example 33).

This composition was also packaged in sealed aluminum tubes. The storage stability of both compositions was monitored; for this purpose, the tubes containing them were left for 72 hours in an oven heated to 100° C.

The tubes were permitted to cool and their contents (and the contents of tubes which had not been subjected to a period of heating, and had been stored for a period of 1 month at ambient temperature) were spread in the form of a layer having a thickness of 2 mm, in the open air, on a polytetrafluoroethylene plate. The deposited layer changed into a rubbery film; 24 hours after the deposition of the layer of elastomer film was removed and the tensile properties of the elastomers were measured after aging for 7 days at ambient temperature.

The results are reported in Table VI below:

TABLE VI

| Tensile properties | EXAMPLE 33 | | EXAMPLE 34 | |
|---|---|---|---|---|
| | Contents of the tubes stored at ambient temperature | Contents of the tubes aged 72 hours at 100° C. | Contents of the tubes stored at ambient temperature | Contents of the tubes aged 72 hours at 100° C. |
| Shore A hardness | 27 | 10 | 26 | — |
| Tensile strength in MPa | 1.1 | 1.0 | 1.0 | — |
| Elongation at break in % | 515 | 450 | 348 | — |

—: not measurable.

Inspection of the values of the tensile properties demonstrated clearly that, in order to retain these properties over time, it is advantageous to employ the catalyst mixture according to the invention rather than di-n-butyltin dilaurate alone.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An organopolysiloxane composition of matter curable into elastomeric state, comprising (1) a curable organopolysiloxane base including an organopolysiloxane polymer and a crosslinking agent therefor, and (2) a catalytically effective amount of a monochelate of pentacoordinated tin of valency IV having the formula:

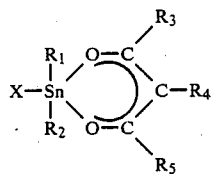

in which:
the symbols R$_1$ and R$_2$, which may be identical or different, are each an optionally substituted, monovalent C$_1$-C$_8$ hydrocarbon radical;
the symbols R$_3$ and R$_5$, which may be identical or different, are each a radical R$_1$ or R$_2$, a hydrogen atom, a C$_1$-C$_5$ alkoxy radical or a silyl radical Si(R$_1$)$_3$;
the symbol R$_4$ is hydrogen atom, or an optionally halogented C$_1$-C$_8$ hydrocarbon radical, with the proviso that R$_4$ and R$_5$ may together form, with the carbon atoms from which they depend, a divalent C$_5$-C 12 cyclic hydrocarbon radical or a substituted such radical bearing at least one chlorine, nitro and/or cyano substituent; and
the symbol X is a monocarboxylate radical of the formula R$_6$COO wherein R$_6$ has the same definition as R$_1$ above 2. An organopolysiloxane composition of matter curable into elastomeric state, comprising (1) a curable organopolysiloxane base including an organopolysiloxane polymer and a crosslinking agent therefor, and (2) a catalytically effective amount of the product of a process for the preparation of a tin monochelate of the formula (1) as defined by claim 1, comprising reacting a tin oxide of the formula:

$$R_1R_2SnO \quad (2)$$

with a $\beta$-dicarbonyl compound of the formula:

$$\begin{array}{c} O \quad H \quad O \\ \parallel \quad | \quad \parallel \\ R_3-C-C-C-R_5 \\ | \\ R_4 \end{array} \quad (3)$$

and with an organic carboxylic acid of the formula:

$$XH \quad (4)$$

and removing the water of reaction.

3. The organopolysiloxane composition as defined by claims 1 or 2 wherein said curable organopolysiloxane base comprises:
(A) 100 parts by weight of an $\alpha,\omega$-dihydroxypolydiorganosiloxane polymer having a viscosity of 500 to 1,000,000 mFa.s and which comprises recurring units of the formula $(R_2)SiO$ where the symbols R, which may be identical or different, are hydrocarbon radicals containing from 1 to 10 carbon atoms, optionally substituted by at least one halogen atom or cyano radical;
(B) 0.5 to 20 parts by weight of an organosilicon compound crosslinking agent containing more than two hydrolyzable groups bonded to silicon atoms, per molecule;
(C) 0 to 250 parts by weight of inorganic filler material; and
(D) 0 to 20 parts by weight of an adhesion promoter.

4. The organopolysiloxane composition as defined by claim 3, comprising a silane crosslinking agent (B) of the formula:

$$R_aSi(Z)_{4-a} \quad (6)$$

in which R is a hydrocarbon radical containing from 1 to 10 carbon atoms and Z is N-substituted amino, N-substituted amido, N,N-disubstituted aminoxy, ketiminoxy, aloxy, aloxyalkylenoxy, enoxy or acyloxy, and a is 0 to 1.

5. The organopolysiloxane composition as defined by claims 1 or 2, in a single-component form.

6. The organopolysiloxane composition as defined by claims 1 or 2, in two-component form.

* * * * *